(12) United States Patent  
Sultanbekov et al.

(10) Patent No.: US 12,230,060 B2
(45) Date of Patent: Feb. 18, 2025

(54) SYSTEM AND METHOD FOR DETERMINING HUMAN EMOTIONS

(71) Applicant: UTEST APP, INC., New York, NY (US)

(72) Inventors: Kanat Sultanbekov, New York, NY (US); Viktor Ivanov, Moscow (RU)

(73) Assignee: Gleenr Inc., New York, NY (US)

( * ) Notice: Subject to any disclaimer, the term of this patent is extended or adjusted under 35 U.S.C. 154(b) by 215 days.

(21) Appl. No.: 17/794,748

(22) PCT Filed: Jan. 22, 2021

(86) PCT No.: PCT/US2021/014536
§ 371 (c)(1),
(2) Date: Jul. 22, 2022

(87) PCT Pub. No.: WO2021/150836
PCT Pub. Date: Jul. 29, 2021

(65) Prior Publication Data
US 2023/0111692 A1    Apr. 13, 2023

Related U.S. Application Data

(60) Provisional application No. 62/964,776, filed on Jan. 23, 2020.

(51) Int. Cl.
*G06V 40/16* (2022.01)
*A61B 5/026* (2006.01)
(Continued)

(52) U.S. Cl.
CPC .......... *G06V 40/174* (2022.01); *A61B 5/0261* (2013.01); *G06V 40/193* (2022.01)

(58) Field of Classification Search
CPC ... G06V 40/174; G06V 40/193; A61B 5/0261
See application file for complete search history.

(56) References Cited

U.S. PATENT DOCUMENTS 10,117,588 B2    11/2018 Lee et al.
10,376,192 B2    8/2019 Lee et al.
(Continued)

OTHER PUBLICATIONS

ISA/US, International Search Report and Written Opinion, PCT/US21/14536, Mar. 31, 2021.

*Primary Examiner* — Alazar Tilahun
(74) *Attorney, Agent, or Firm* — John H. Choi & Associates (57) ABSTRACT

The present invention provides a system and method for determining human emotions. The system includes an input device for receiving at least one image of a human face and at least one processor for: processing the at least one image to generate a heat map of the at least one image as a first identifying data; processing the heat map to generate a second identifying data relating to emotional conditions based on heat; processing the at least one image to generate a third identifying data relating to emotional conditions based on muscle movement; and processing the at least one image to generate a fourth identifying data relating to truthfulness. The first, second, third and fourth identifying data are then collectively processed to generate a final emotion identifier for display on an output device.

23 Claims, 5 Drawing Sheets (51) Int. Cl.
*G06V 40/18* (2022.01)
*G06V 40/19* (2022.01)

(56) References Cited

U.S. PATENT DOCUMENTS

| | | |
|---|---|---|
| 10,694,988 B2 | 6/2020 | Lee et al. |
| 2016/0098592 A1* | 4/2016 | Lee .................. G06F 18/24155 434/236 |
| 2016/0360970 A1 | 12/2016 | Tzvieli et al. |
| 2019/0384392 A1* | 12/2019 | Aimone ................ G09G 3/003 |

* cited by examiner

SYSTEM AND METHOD FOR DETERMINING HUMAN EMOTIONS

CROSS-REFERENCE TO RELATED APPLICATION

This application claims priority to U.S. Provisional Application No. 62/964,776, filed on Jan. 23, 2020, titled "System and Method for Determining Human Emotions," which is incorporated by reference in its entirety.

FIELD

The present disclosure relates to human data processing and in particular to a system and method for determining human emotions from captured human data.

BACKGROUND

Identifying human emotions has become an important factor in many areas of life. For example, for use in security systems, the near-instant detection or selection of potential terrorists from among crowds of people in highly concentrated public areas could be determined from identifying the emotions of people in the crowds, such as at airports, train and bus stations, and at security booths of public institutions and large corporate facilities.

Similarly, law enforcement agencies would value the identification of human emotions during criminal interrogations, as well as for crime prevention, in which human emotions are determined from captured camera images. Accordingly, some crimes such as premeditated murder with its negative human emotional states may be prevented by determining such negative emotional states in advance of commitment of such crimes.

Further uses of the identification of human emotions include the determination of an emotional mood of a person for the purpose of advertising, by which sales specialists in, for example, shopping centers or stores can select people who are the most willing to purchase specific products, to analyze the reactions of people to advertising, and to create more effective advertising strategies.

The identification of human emotions also finds use in the entertainment industry, such as in the development of computer games controlled by human emotions or by the use of emotion recognition as a separate element of gameplay. Similarly, identification of human emotion facilitates the use of social networks, such as for the automatic generation of emoticons, the correlation of real facial expressions of a social network user with an overlay image, and the use in determining a mask in a special image filter.

Other business applications of the identification of human emotions include increasing the effectiveness of analysis of a job candidate during an interview for an employment position, as well as an analysis of the emotional mood of business partners. Similarly, applications in banking include determining the truthfulness of a potential borrower of money, as well as identifying difficult employees. Further applications in everyday life of the identification of human emotions include the identification of adultery in relationships or the commission of other significant misconduct.

In the prior art, the identification of human emotions has been performed using inaccurate devices such as polygraphs. In addition, such prior art devices often require the use of human operators to administer and interpret such identification of human emotions.

Accordingly, a need exists for an accurate and automated system and method for identifying human emotions.

In addition, such devices in the prior art for identifying human emotions, including polygraphs, require physical contact between the devices and the person being evaluated.

Accordingly, a need exists for a system and method which identifies human emotions without the need for actual physical contact with the subject being evaluated.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In general, the present invention provides system and method use images of an object, such as a human, with the images captured by a camera. The images are processed utilizing artificial neural networks to generate and output an emotion identifier corresponding to an emotional condition of the object.

In one aspect, the present invention provides a system comprising: an input device for receiving at least one image of a human face; a transdermal imaging processor, executing at least one predetermined software application, for processing the at least one image by: mapping topography of blood vessels and muscles underlying exposed skin and tissues of the human face based on light reflected in the at least one image, applying a digital monochrome filter to remove red, green and blue colors from the at least one image to determine hemoglobin movement intensity, and applying a digital heat filter to generate a heat map of the at least one image as a first identifying data; a heat map processor, executing the at least one predetermined software application, for processing the heat map by comparing the heat map with an emotional condition database to generate a second identifying data, wherein the emotional condition database comprises a plurality of predetermined emotional conditions corresponding to respective predetermined heat patterns of a human; a facial muscle processor, executing the at least one predetermined software application, for processing the at least one image by comparing the at least one image with a motion unit database to generate a third identifying data, the motion unit database comprising a plurality of predetermined motion units corresponding to respective predetermined motion unit numbers, and predetermined degrees of intensity; an oculomotor reaction processor, executing the at least one predetermined software application, for processing the at least one image by comparing the at least one image with an oculomotor database to generate a fourth identifying data, the oculomotor database comprising a plurality of oculomotor parameters corresponding to respective oculomotor characteristics to determine a characteristic of truthfulness; a main processor, executing the at least one predetermined software application, for receiving and processing the first, second, third and fourth identifying data, and generating a final emotion identifier; and an output device for receiving and displaying the final emotion identifier.

In another aspect, the present invention provides a method comprising the steps of: capturing at least one image of a human face with an input device; executing at least one predetermined software application using a transdermal imaging processor for processing the at least one image by: mapping topography of blood vessels and muscles underlying exposed skin and tissues of the human face based on light reflected in the at least one image, applying a digital monochrome filter to remove red, green and blue colors from the at least one image to determine hemoglobin movement intensity, and applying a digital heat filter to generate a heat map of the at least one image as a first identifying data; executing the at least one predetermined software application using a heat map processor for processing the heat map by comparing the heat map with an emotional condition database to generate a second identifying data, wherein the emotional condition database comprises a plurality of predetermined emotional conditions corresponding to respective predetermined heat patterns of a human; executing the at least one predetermined software application using a facial muscle processor for processing the at least one image by comparing the at least one image with a motion unit database to generate a third identifying data, the motion unit database comprising a plurality of predetermined motion units corresponding to respective predetermined motion unit numbers, and predetermined degrees of intensity; executing the at least one predetermined software application using an oculomotor reaction processor, for processing the at least one image by comparing the at least one image with an oculomotor database to generate a fourth identifying data, the oculomotor database comprising a plurality of oculomotor parameters corresponding to respective oculomotor characteristics to determine a characteristic of truthfulness; executing the at least one predetermined software application using a main processor for receiving and processing the first, second, third and fourth identifying data, and generating a final emotion identifier; and receiving and displaying the final emotion identifier on an output device.

In yet another aspect, the present invention provides a non-transitory computer readable medium storing instructions executable by a processor, the stored instructions implementing a method comprising the steps of: receiving, at an input device, at least one image of a human face; executing, by a processor, a predetermined program for determining human emotions by: processing the at least one image by: mapping topography of blood vessels and muscles underlying exposed skin and tissues of the human face based on light reflected in the at least one image, applying a digital monochrome filter to remove red, green and blue colors from the at least one image to determine hemoglobin movement intensity, and applying a digital heat filter to generate a heat map of the at least one image as a first identifying data, processing the heat map by comparing the heat map with an emotional condition database to generate a second identifying data, wherein the emotional condition database comprises a plurality of predetermined emotional conditions corresponding to respective predetermined heat patterns of a human, processing the at least one image by comparing the at least one image with a motion unit database to generate a third identifying data, the motion unit database comprising a plurality of predetermined motion units corresponding to respective predetermined motion unit numbers, and predetermined degrees of intensity, processing the at least one image by comparing the at least one image with an oculomotor database to generate a fourth identifying data, the oculomotor database comprising a plurality of oculomotor parameters corresponding to respective oculomotor characteristics to determine a characteristic of truthfulness, and receiving and processing the first, second, third and fourth identifying data, and generating a final emotion identifier; and outputting, at an output device, the final emotion identifier.

BRIEF DESCRIPTION OF DRAWINGS

The foregoing summary, as well as the following detailed description of presently preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

To facilitate an understanding of the invention, identical reference numerals have been used, when appropriate, to designate the same or similar elements that are common to the figures. Further, unless stated otherwise, the features shown in the figures are not drawn to scale, but are shown for illustrative purposes only.

DETAILED DESCRIPTION

Certain terminology is used in the following description for convenience only and is not limiting. The article "a" is intended to include one or more items, and where only one item is intended the term "one" or similar language is used. Additionally, to assist in the description of the present invention, words such as top, bottom, side, upper, lower, front, rear, inner, outer, right and left may be used to describe the accompanying figures. The terminology includes the words above specifically mentioned, derivatives thereof, and words of similar import.

Figure 1:
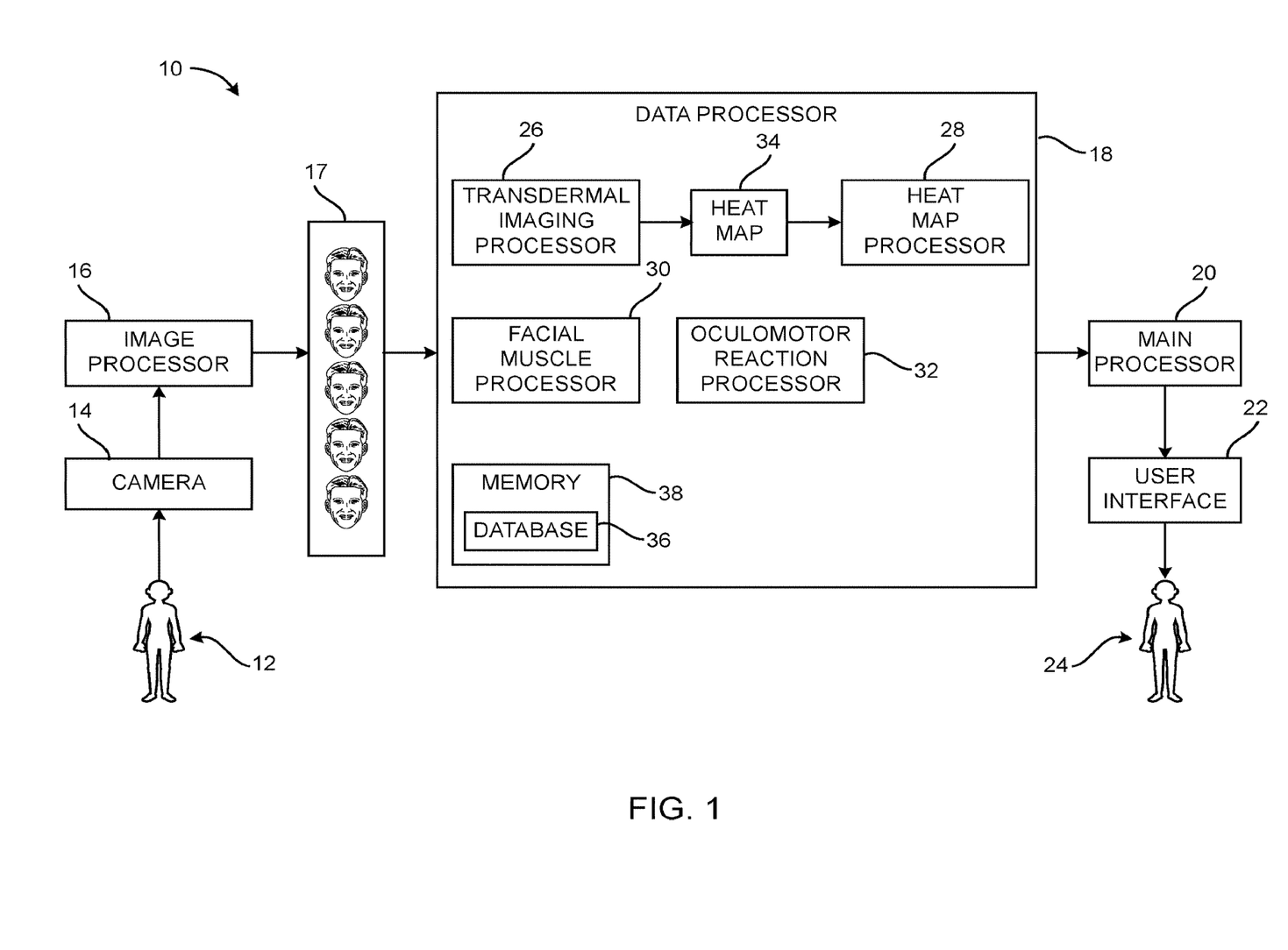
FIG. 1 illustrates a system of the present invention.
Figure 6:
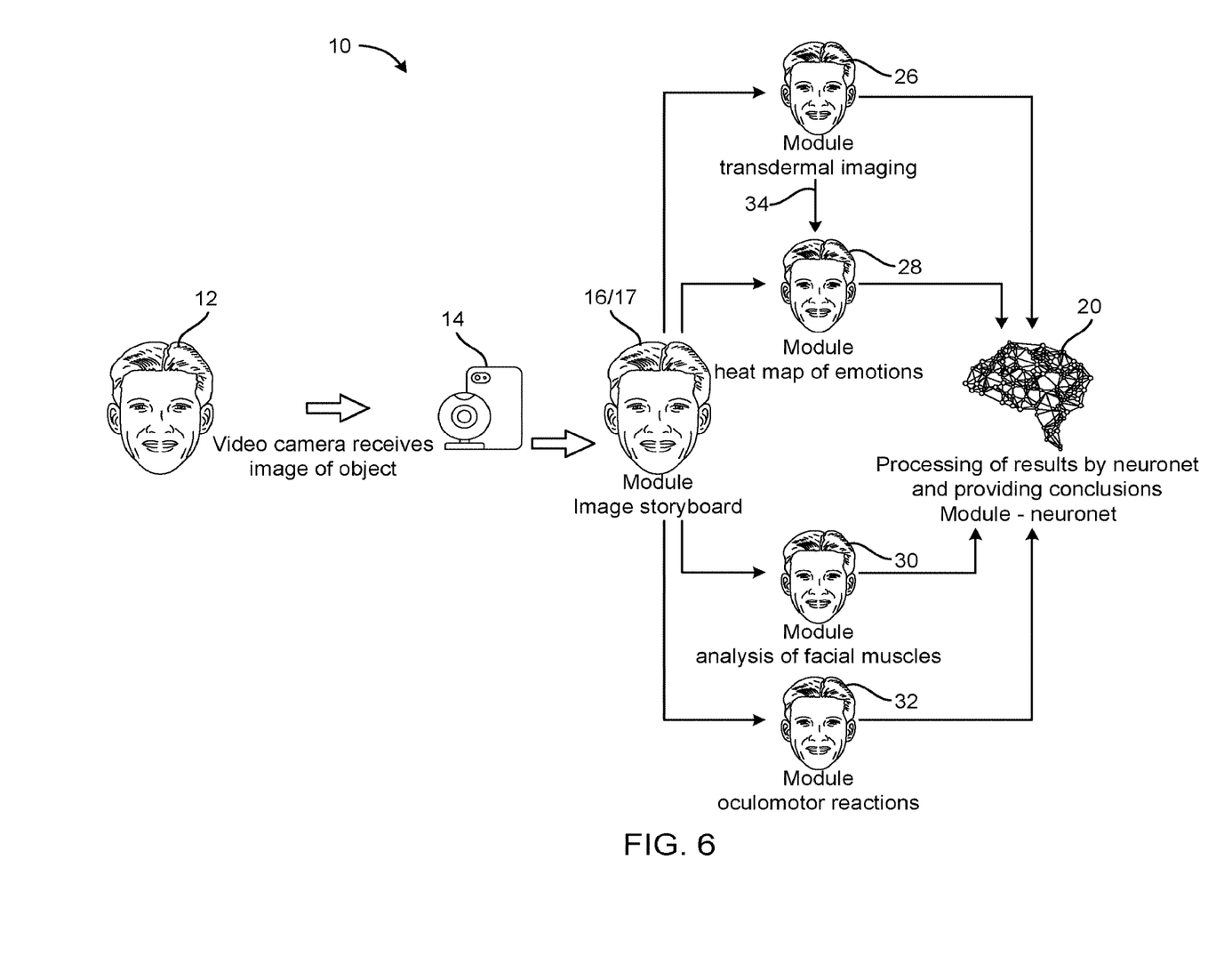
FIG. 6 further illustrates the system of the present invention.

The present invention provides a system 10 for identifying an emotional condition of a object 12, such as a human. As shown in FIGS. 1 and 6, in general, the system 10 includes a plurality of modules that process and generate data from a captured image of an object 12. First, the captured image is initially processed and at least one static image 17 is generated by an image storyboard module or image processor 16. The static images are then further processed by the secondary modules, namely, a transdermal imaging processor 26, a heat map processor 28, a facial muscle processor 30 and an oculomotor reaction processor 32 for: transdermal imaging; heat mapping; analysis of facial muscles; and oculomotor reactions, respectively. In turn data is generated by each secondary module and the data is then transmitted to and further processed on a neuronet module by a main processor 20 for providing conclusions.

As shown in FIGS. 1 and 6, a video footage and/or a static or still image of the object 12, in this instance a human face, is captured using an input device or camera 14, and the image is conveyed by the image processor 16 to a data processor 18. The camera 14 may be, for example, an 8 mega pixel camera with autofocus. Preferably, the camera 14 is not less than 8 mega pixels with autofocus and the distance to the human face is not more than 60 centimeters from the camera 14. For subsequent processing by the system 10, the camera 14 preferably captures a plurality of static images 17 of the object 12 over a period of time. Alternatively, the camera 14 may be a video camera which captures a plurality of images of the human face 12 over a period of time such as a sequence of interconnected frames or static images as a video. If a video is captured by the camera 14, the image processor 16 generates a plurality of static images 17 and storyboards the generated static images, which is then conveyed to the data processor 18. The captured images are then further processed by the data processor 18, which generates identifying data utilized by a main processor 20 to generate a final emotion identifier in, for example, a text message sent to a user interface of an output device 22 for output to a user 24 of the system 10.

In an example embodiment, as shown in FIGS. 1 and 6, the data processor 18 further includes at least one sub-processor, such as a transdermal imaging processor 26, a heat map processor 28, a facial muscle processor 30, and an oculomotor reaction processor 32, with each processor described in greater detail below. The processors 26-32 may operate independently and concurrently, for example, in parallel. The components 14-22 of the system 10, including the at least one processor 26-32 of the data processor 18, may be cloud-based and/or interconnected via at least one network such as the Internet. Alternatively, the system 10 may be a stand-alone system of interconnected components having, for example, 1024 Mb of RAM, 500 Mb of memory in the form of a hard disk drive, and dual core CPUs operating at 1.7 Hz. The system 10 operates software, such as add-in applications, to run the processors 16-20, 26-32 as well as the user interface 22, and uses an operating system such as ANDROID 5.2, iOS 8, WINDOWS XP, LINUX, or macOS 10.10. Some of the components of the system 10 utilize trained artificial neural networks, as described below, such as NEON neural networks available from NERVANA SYSTEMS or neural networks available from CAFFE.

Figure 2:
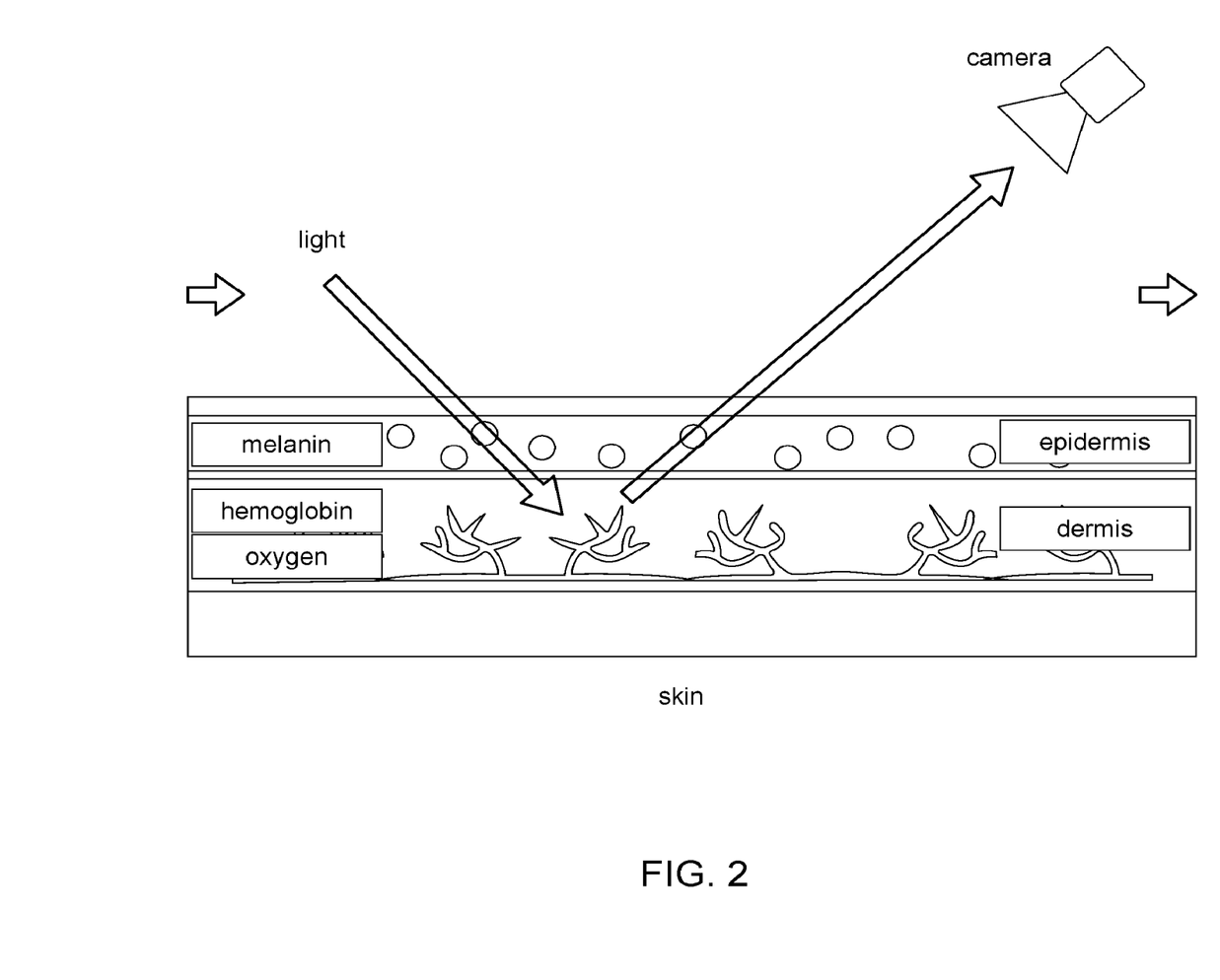
FIG. 2 illustrates the reflection of light radiation by skin or tissue.

The transdermal imaging processor 26 filters the captured image from the image processor 16 to obtain an image layer which corresponds to a thermal picture of biochemical reactions occurring in the human body and/or the object 12 within the captured image, and without the use of special hardware such as infrared sensors. Instead, the transdermal imaging processor 26 processes light radiation reflected from the human body, as shown in FIG. 2. Since the epidermis layer of the skin at least partially transmits light, such as from the exposed face and other unclothed areas of the human body, the streaming light radiation reflected from the human body or skin contains data regarding the conditions of the underlying layers of skin and/or tissues. For example, melanin and hemoglobin have distinct color signatures which are detected in and selected from the received light. The transdermal imaging processor 26 determines the thickness and intensity of fluid flow in the capillaries of the skin and/or tissues, such as in the face of the object 12.

Using a digital monochrome filter applied to the captured image of the received light, the transdermal imaging processor 26 maps the topography of the blood vessels and muscles underlying the exposed skin and tissues, such as the exposed areas of the face or body of the object 12, and so an emotion intensity map is built from the mapped topography. Such processing of the captured image is described in J. Liu et al., "Transdermal optical imaging revealed different spatiotemporal patterns of facial cardiovascular activities", NATURE, SCI REP 8, 10588 (2018) doi:10.1038/s41598-018-28804-0, retrieved at https://www.nature.com/articles/s41598-018-28804-0.

During such mapping of the topography, the transdermal imaging processor 26 applies the digital monochrome filter to perform recombination of bit layers of the captured image. The digital monochrome filter bleaches the main RGB channel of the reflected light from the object 12, which is initially received by the camera 14. Thus, all three colors of red, green, and blue are removed, leaving the dark colors of black and gray which represent the intensity of the blood and hemoglobin flowing at the exposed parts of the object 12, such as the face and/or body of the object 12. Furthermore, due to the differences in intensities, data is obtained which represents the hemoglobin movement intensity, and the quantity of hemoglobin at specific areas of the face and skin. Accordingly, lower temperatures represent lower rates of the presence and flow of hemoglobin, while higher temperatures represent higher rates of the presence and flow of hemoglobin. Using additional biological data such as the heartbeat and temperature of the object 12, a neural network is used to perform corrections in the movement intensity. The digital monochrome filter acts as a pyrometer which is software-based, using a neural network and other biological data from a live object 12 with exposed facial and/or body areas.

The digital monochrome filter also acts as a digital heat filter to decrypt the movement intensity of the components of blood flowing in the object 12. By acting as a digital heat filter, the digital monochrome filter generates a heat map 34 of the object 12, which is conveyed to the heat map processor 28. The heat map 34 corresponds to the emotion intensity map derived from the actual location of the blood vessels in the exposed areas of the skin and/or tissues. The heat map 34 is output by the transdermal imaging processor 26 as first identifying data utilized by the main processor 20, as described in greater detail below.

The heat map processor 28 processes the captured image from the image processor 16 in conjunction with the heat map 34 to generate second identifying data utilized by the main processor 20, as described in greater detail below. The captured image is used as a guide to match portions of the heat map 34 to the shape of the object 12 in reference images stored in a database 36 in a memory 38 of the data processor 18.

Figure 3:
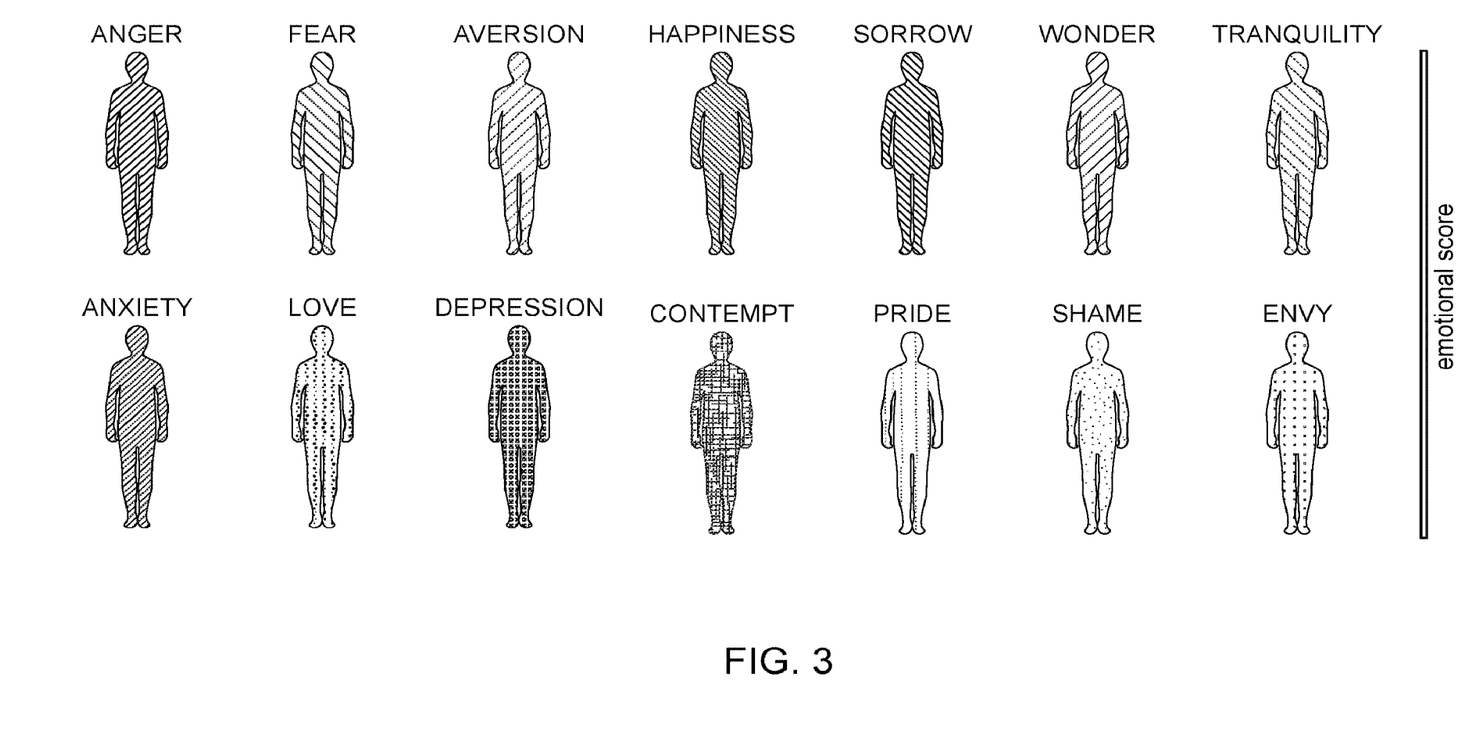
FIG. 3 illustrates example reference images corresponding to common emotional conditions.

Accordingly, the heat map 34 is compared with the reference images corresponding to the manifestation of certain human emotions. Such reference images are obtained by research known in the prior art, and the reference images reflect the relationship among at least 27 of the most common emotional conditions of humans and the biochemical processes that accompany the manifestation of such emotional conditions, including anger, fear, aversion, happiness, sorrow, wonder, tranquility, anxiety, love, depression, contempt, pride, shame, and envy. Examples of the reference images are shown in FIG. 3 and are found through Nummenmaa Lab at http://emotion.utu.fi.

The heat map processor 28 utilizes a trained neural network to determine a degree of compliance between the reference images from the database and the heat map 34 received from the transdermal imaging processor 26. The degree of compliance, which may be measured as a percentage value, is the second identifying data utilized by the main processor 20, as described in greater detail below.

The facial muscle processor 30 classifies features in the captured image from the image processor 16 to generate third identifying data utilized by the main processor 20, as described in greater detail below. The captured image is processed using known facial recognition methods to determine an area corresponding to the face of the object 12, and the area is highlighted on the original captured image.

The portions of the captured image corresponding to the identified area are applied to a trained neural network to identify manifested emotions by the determination of motion units and involved muscles of the human face of the object 12. There may be 41 motion units on the human face according to the Facial Action Coding System (FACS) in the prior art, from which emotions can be determined by the trained neural network according to the known Emotion Facial Action Coding System (EmFACS) in the prior art. The FACS and EmFACS are due in part to the work originally developed by Carl-Herman Hjortsjo, which was later adopted by Paul Ekman and Wallace V. Friesen, and published in 1978. The 41 motion units on the human face are directly controlled by the central nervous system. Briefly manifested emotions, which may last less than ⅕ of a second, may be difficult for humans alone to identify, but such briefly manifested emotions are well recognized by a trained neural network. Examples of motion units (MUs) and their basic codes are shown in Table 1 below, which are responsible for the manifestation of emotions:

TABLE 1

| MU No. | Facial Motion Unit Name |
| --- | --- |
| 0 | Neutral Face |
| 1 | Eyebrow Internal Part Lift |
| 2 | Eyebrow External Part Lift |
| 4 | Eyebrow Lowered |
| 5 | Upper Eyelid Lift |
| 6 | Cheek Lift |
| 7 | Eyelid Tensioner |
| 8 | Lips Towards Each Other |
| 9 | Nose Wrinkler |
| 10 | Upper Lip Lift |
| 11 | Nasolabial Folds Deepener |
| 12 | Lip Corner Lift |
| 13 | Sharp Lip Corner Lift |
| 14 | Dimple |
| 15 | Lip Corner Lowered |
| 16 | Lower Lip Lowered |
| 17 | Chin Lift |
| 18 | Lips Wrinkler |
| 19 | Tongue Exposure |
| 20 | Lips Stretcher |
| 21 | Neck Tensioner |
| 22 | Funnel Lips |
| 23 | Lips Tensioner |
| 24 | Lips Squeezer |
| 25 | Lips Apart |
| 26 | Jaw Down |
| 27 | Mouth Widely Open |
| 28 | Lips Retraction |
| 29 | Lower Jaw Forward |
| 30 | Jaw Sideways |
| 31 | Jaw Clamping |
| 32 | Lip Biting |
| 33 | Blowing |
| 34 | Blowing Cheeks |
| 35 | Squeeze Cheeks In |
| 36 | Tongue Out |

TABLE 1-continued

| MU No. | Facial Motion Unit Name |
| --- | --- |
| 37 | Lips Licking |
| 38 | Nostril Expansion |
| 39 | Nostril Narrowing |
| 41 | Nose Bridge Top Lowered |
| 42 | Eyebrow Internal Lowered |
| 43 | Eyes Closed |
| 44 | Eyebrows Furrowed |
| 45 | Blinking |
| 46 | Wink |

Additional motion units with associated MU codes are directed to other body parts related to facial and emotion recognition, as described in Table 2 below:

TABLE 2

| MU No. | Facial Motion Unit Name Describing Head Motion | MU No. | Facial Motion Unit Name Describing Head Motion |
| --- | --- | --- | --- |
| 51 | Head Turn Left | 61 | Eyes Abduction Left |
| 52 | Head Turn Right | M61 | Eyes Left |
| 53 | Head Up | 62 | Eyes Abduction Right |
| 54 | Head Down | M62 | Eyes Right |
| 55 | Head Tilt Left | 63 | Eyes Up |
| M55 | Head Tilt Left | 64 | Eyes Down |
| 56 | Head Tilt Right | 65 | Exotropia |
| M56 | Head Tilt Right | 66 | Esotropia |
| 57 | Head Forward | M68 | Eyes Rolling |
| M57 | Head Push Forward | 69 | Eyes on Another Person |
| 58 | Head Back | M69 | Head and/or Eyes on Another Person |
| M59 | Nod Head | | |
| M60 | Head Side to Side | | |
| M83 | Head Up and Side | | |

Any code for a motion unit may be characterized by a different degree of intensity of manifestation, such as with an accompanying "A" for weakly expressed, an accompanying "B" for slightly expressed, an accompanying "C" for noticeably expressed, an accompanying "D" for strongly expressed, and an accompanying "E" for extremely expressed. In addition, a code for a motion unit having a preceding "M" indicates a micro-expression, while a preceding "U" indicates a symmetrical expression. Furthermore, an asterisk, star, or "*" next to a code for a motion unit indicates the possibility of adjustment of an internal value of the motion unit as evaluated in the system 10.

Accordingly, basic emotions can be expressed in patterns, which are composed of one or more motion units, in various degrees of severity. Example patterns are shown in Table 3 below:

TABLE 3

| Emotion | Pattern | Emotion | Pattern |
|---|---|---|---|
| Anger | 4 + 5* + 7 + 10* + 22 + 23 + 25 or 26 | Contempt | 9 or U10 |
|  | 4 + 5* + 7 + 10* + 23 + 25 or 26 |  | 12 |
|  | 4 + 5* + 7 + 23 + 25 or 26 |  | U14 or B14 |
|  | 4 + 5* + 7 + 17 + 23 |  |  |
|  | 4 + 5* + 7 + 17 + 24 |  |  |
|  | 4 + 5* + 7 + 23 |  |  |
|  | 4 + 5* + 7 + 24 |  |  |
| Sorrow | 1 + 4 + 11 + 15B with/without 54 + 64 | Fear | 1 + 2 + 4 + 5* + 20 ++ 25, 26, or 27 |
|  | 1 + 4 + 15* with/without 54 + 64 |  | 1 + 2 + 4 + 5* + 25, 26, or 27 |
|  | 6 + 15* with/without 54 + 64 |  |  |
| Joy | 6 + 12* | Aversion | 9 |
|  | 12C/D |  | 9 + 16 + 15 or 26 |
|  |  |  | 9 + 17 |
|  |  |  | 10* |
|  |  |  | 10* + 16 + 25 or 26 |
|  |  |  | 10 + 17 |
| Wonder | 1 + 2 + 5B + 26 |  |  |
|  | 1 + 2 + 5B + 27 |  |  |

The facial muscle processor 30 uses a neural network to identify the motion units from the features of the area corresponding to a human face of the object 12, and so outputs the identified motion units which are further processed to determine a corresponding emotion using the combinations of motion units in Table 3. The corresponding emotion is the third identifying data utilized by the main processor 20, as described in greater detail below.

Figure 4:
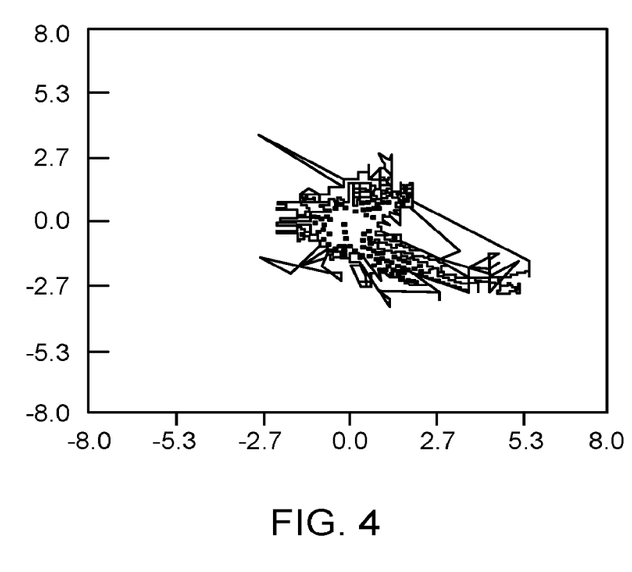
FIG. 4 illustrates a plot of eye movement trajectories corresponding to a truthful state.
Figure 5:
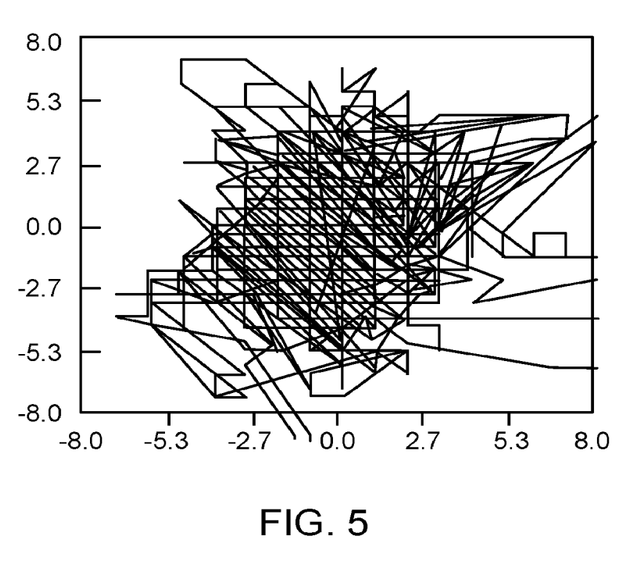
FIG. 5 illustrates a plot of eye movement trajectories corresponding to a falsehood state.

The oculomotor reaction processor 32 classifies the captured image from the image processor 16 to generate fourth identifying data utilized by the main processor 20, as described in greater detail below. The oculomotor reaction processor 32 first identifies an area of the captured image corresponding to the eyes of the object 12, using facial recognition methods known in the art, and highlights the identified eye area in the captured image. The oculomotor reaction processor 32 then utilizes a direct relation of activity of the central nervous system with a plurality of parameters, including gaze direction dynamics or movement trajectory, the size of the pupils of the eyes, and the number of eye blinks in Table 4 below:

Table 4 above shows a correlation matrix reflecting the individual parameter dynamics which change when the human as the object 12 utters a false statement. Such a determination of the activity of the central nervous system indirectly allows the oculomotor reaction processor 32 to determine the emotional condition of the human in the captured image during communication of the human as the object 12 with others. The oculomotor reaction processor 32 applies the parameters to the neural network, which compares the parameters with main patterns, as shown in FIGS. 4-5, which describe the signs of true or false statements, respectively, and which generates an indication of a true or false statement as fourth identifying data utilized by the main processor 20, as described in greater detail below. For example, when measured horizontal and vertical eye movements are plotted, there is a high correlation that the plotted eye movements will be generally centrally located, as shown in FIG. 4, indicating the object 12 is being truthful. However, as shown in Table 4, there is only a 0.371429 correlation value when measured horizontal and vertical eye movements are plotted, indicating that the plotted eye movements will not be generally centrally located, as shown in

TABLE 4

| Parameters | Number of Blinks | Pupil Size Fluctuation Amplitude | Min. Pupil Size | Max. Pupil Size | Horizontal Eye Movement | Vertical Eye Movement | Scanned Area |
|---|---|---|---|---|---|---|---|
| Number of Blinks | 1 |  |  |  |  |  |  |
| Pupil Size Fluctuation Amplitude | −0.085714 | 1 |  |  |  |  |  |
| Min. Pupil Size | 0.057977 | 0.985611 | 1 |  |  |  |  |
| Max. Pupil Size | 0.371429 | 0.885714 | 0.927 | 1 |  |  |  |
| Horizontal Eye Movement | −0.20000 | 0.542857 | 0.579 | 0.314 | 1 |  |  |
| Vertical Eye Movement | −0.142857 | 0.828571 | 0.811 | 0.714 | 0.371429 | 1 |  |
| Scanned Area | −0.371429 | 0.885714 | 0.840 | 0.657 | 0.485714 | 0.885714 | 1 |

FIG. 5, indicating that the human as the object 12 is being false. The oculomotor reaction processor 32 then takes the truth or falsehood values and outputs such values as fourth identifying data utilized by the main processor 20, as described in greater detail below.

The main processor 20 receives the heat map 34 corresponding to an emotion intensity map as the first identifying data, receives the degree of compliance with heat-based reference images of emotions as the second identifying data, receives the facial emotion corresponding to detected motor units as the third identifying data, and receives the truth or falsehood values as the fourth identifying data from the data processor 18. The main processor 20 applies such first, second, third, and fourth identifying data to a trained neural network to classify the emotion of the object 12 using weight or significance coefficients of neurons as determined during the training process. By weighting the heat map 34, the degree of compliance, the determined facial emotion, and the truth or falsehood values, the neural network of the main processor 20 generates a final emotion identifier representing the emotional condition of the object 12. The main processor 20 also determines a percentage of accuracy of the conclusion of processing by the neural network to generate the final emotion identifier.

In turn, the main processor 20 generates a text message from the final emotion identifier sent to the user interface of the output device 22 for output to the user 24. The user interface 22 may be any output device, such as a display or printer, for outputting the text message indicating the emotional condition of the object 12.

Each module for processing the images could have its own software application but a single software application or a non-transitory computer readable medium could run parts of or the entire system as well. Moreover, even though the present invention is described as having a plurality of processors, one of ordinary skill in the art will recognize that the system could have a single processor for executing the steps of the method described herein.

The present invention may be embodied in other specific forms without departing from its spirit or essential characteristics. The described embodiments are to be considered in all respects only as illustrative and not restrictive. The scope of the invention, therefore, will be indicated by claims rather than by the foregoing description. All changes, which come within the meaning and range of equivalency of the claims, are to be embraced within their scope.

The invention claimed is:

1. A system comprising:
    an input device for receiving at least one image of a human face;
    a transdermal imaging processor, executing at least one predetermined software application, for processing the at least one image by: mapping topography of blood vessels and muscles underlying exposed skin and tissues of the human face based on light reflected in the at least one image, applying a digital monochrome filter to remove red, green and blue colors from the at least one image to determine hemoglobin movement intensity, and applying a digital heat filter to generate a heat map of the at least one image as a first identifying data;
    a heat map processor, executing the at least one predetermined software application, for processing the heat map by comparing the heat map with an emotional condition database to generate a second identifying data, wherein the emotional condition database comprises a plurality of predetermined emotional conditions corresponding to respective predetermined heat patterns of a human;
    a facial muscle processor, executing the at least one predetermined software application, for processing the at least one image by comparing the at least one image with a motion unit database to generate a third identifying data, the motion unit database comprising a plurality of predetermined motion units corresponding to respective predetermined motion unit numbers, and predetermined degrees of intensity;
    an oculomotor reaction processor, executing the at least one predetermined software application, for processing the at least one image by comparing the at least one image with an oculomotor database to generate a fourth identifying data, the oculomotor database comprising a plurality of oculomotor parameters corresponding to respective oculomotor characteristics to determine a characteristic of truthfulness;
    a main processor, executing the at least one predetermined software application, for receiving and processing the first, second, third and fourth identifying data, and generating a final emotion identifier; and
    an output device for receiving and displaying the final emotion identifier.

2. The system of claim 1, further comprising an image processor, executing the at least one predetermined software application, for processing the at least one image captured by video and generating at least one static image.

3. The system of claim 1, wherein the plurality of emotional conditions is selected from a group comprising: anger, fear, aversion, happiness, sorrow, wonder, tranquility, anxiety, love, depression, contempt, pride, shame and envy.

4. The system of claim 1, wherein the motion units are movements on a human face and a human head.

5. The system of claim 1, wherein the motion unit database further comprises predetermined emotional conditions corresponding to predetermined patterns based on combinations of motion unit numbers and degrees of intensity.

6. The system of claim 1, wherein the oculomotor characteristics are characteristics and movements of a human eye.

7. A method comprising the steps of:
    capturing at least one image of a human face with an input device;
    executing at least one predetermined software application using a transdermal imaging processor for processing the at least one image by: mapping topography of blood vessels and muscles underlying exposed skin and tissues of the human face based on light reflected in the at least one image, applying a digital monochrome filter to remove red, green and blue colors from the at least one image to determine hemoglobin movement intensity, and applying a digital heat filter to generate a heat map of the at least one image as a first identifying data;
    executing the at least one predetermined software application using a heat map processor for processing the heat map by comparing the heat map with an emotional condition database to generate a second identifying data, wherein the emotional condition database comprises a plurality of predetermined emotional conditions corresponding to respective predetermined heat patterns of a human;
    executing the at least one predetermined software application using a facial muscle processor for processing the at least one image by comparing the at least one image with a motion unit database to generate a third identifying data, the motion unit database comprising a plurality of predetermined motion units corresponding to respective predetermined motion unit numbers, and predetermined degrees of intensity;

executing the at least one predetermined software application using an oculomotor reaction processor, for processing the at least one image by comparing the at least one image with an oculomotor database to generate a fourth identifying data, the oculomotor database comprising a plurality of oculomotor parameters corresponding to respective oculomotor characteristics to determine a characteristic of truthfulness;

executing the at least one predetermined software application using a main processor for receiving and processing the first, second, third and fourth identifying data, and generating a final emotion identifier; and receiving and displaying the final emotion identifier on an output device.

8. The method of claim 7, wherein the at least one image is captured by video.

9. The method of claim 8, further comprising the step of executing the at least one predetermined software application using an image processor for processing the at least one image captured by video and generating at least one static image.

10. The method of claim 7, wherein the plurality of emotional conditions is selected from a group comprising: anger, fear, aversion, happiness, sorrow, wonder, tranquility, anxiety, love, depression, contempt, pride, shame and envy.

11. The method of claim 7, wherein the motion units are movements on a human face and a human head.

12. The method of claim 7, wherein the motion unit database further comprises predetermined emotional conditions corresponding to predetermined patterns based on combinations of motion unit numbers and degrees of intensity.

13. The method of claim 7, wherein the oculomotor characteristics are characteristics and movements of a human eye.

14. A non-transitory computer readable medium storing instructions executable by a processor, the stored instructions implementing a method comprising the steps of:

receiving, at an input device, at least one image of a human face;

executing, by a processor, a predetermined program for determining human emotions by:

processing the at least one image by: mapping topography of blood vessels and muscles underlying exposed skin and tissues of the human face based on light reflected in the at least one image, applying a digital monochrome filter to remove red, green and blue colors from the at least one image to determine hemoglobin movement intensity, and applying a digital heat filter to generate a heat map of the at least one image as a first identifying data, processing the heat map by comparing the heat map with an emotional condition database to generate a second identifying data, wherein the emotional condition database comprises a plurality of predetermined emotional conditions corresponding to respective predetermined heat patterns of a human, processing the at least one image by comparing the at least one image with a motion unit database to generate a third identifying data, the motion unit database comprising a plurality of predetermined motion units corresponding to respective predetermined motion unit numbers, and predetermined degrees of intensity, processing the at least one image by comparing the at least one image with an oculomotor database to generate a fourth identifying data, the oculomotor database comprising a plurality of oculomotor parameters corresponding to respective oculomotor characteristics to determine a characteristic of truthfulness, and receiving and processing the first, second, third and fourth identifying data, and generating a final emotion identifier; and outputting, at an output device, the final emotion identifier.

15. The non-transitory computer readable medium of claim 14, wherein the at least one image is captured by video.

16. The non-transitory computer readable medium of claim 15, further comprising the step of processing the at least one image captured by video and generating at least one static image.

17. The non-transitory computer readable medium of claim 15, wherein the plurality of emotional conditions is selected from a group comprising: anger, fear, aversion, happiness, sorrow, wonder, tranquility, anxiety, love, depression, contempt, pride, shame and envy.

18. The non-transitory computer readable medium of claim 15, wherein the motion units are movements on a human face and a human head.

19. The non-transitory computer readable medium of claim 15, wherein the motion unit database further comprises predetermined emotional conditions corresponding to predetermined patterns based on combinations of motion unit numbers and degrees of intensity.

20. The non-transitory computer readable medium of claim 15, wherein the oculomotor characteristics are characteristics and movements of a human eye.

21. The system of claim 1, wherein the input device is non-wearable.

22. The method of claim 7, wherein the input device is non-wearable.

23. The non-transitory computer readable medium of claim 14, wherein the input device is non-wearable.

* * * * *